US00PP32891P2

(12) United States Plant Patent
Bisschop et al.

(10) Patent No.: US PP32,891 P2
(45) Date of Patent: Mar. 9, 2021

(54) ***RUDBECKIA* PLANT NAMED 'ET RDB 18-30'**

(50) Latin Name: ***Echinacea purpurea* X *Rudbeckia hirta***
Varietal Denomination: ET RDB 18-30

(71) Applicants: Elisabeth Bisschop, Boijl (NL); Bart Noordhuis, Boijl (NL)

(72) Inventors: Elisabeth Bisschop, Boijl (NL); Bart Noordhuis, Boijl (NL)

(73) Assignee: ETERNAL PLANT BOIJL B.V., Boijl (NL)

( * ) Notice: Subject to any disclaimer, the term of this patent is extended or adjusted under 35 U.S.C. 154(b) by 0 days.

(21) Appl. No.: 16/873,596

(22) Filed: May 14, 2020

(30) Foreign Application Priority Data

Nov. 4, 2019 (QZ) ..... PBR 2019/2797

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 6/14
See application file for complete search history.

*Primary Examiner* — Anne Marie Grunberg
(74) *Attorney, Agent, or Firm* — C. Anne Whealy

(57) ABSTRACT

A new and distinct cultivar of *Rudbeckia* plant named 'ET RDB 18-30', characterized by its relatively compact, upright to somewhat outwardly spreading and mounded plant habit; dense and bushy growth habit; freely flowering habit; long-lasting single-type inflorescences with yellow orange and dark red bi-colored ray florets positioned above the foliar plane on strong peduncles; and good postproduction and garden performance.

2 Drawing Sheets

Figure 1:
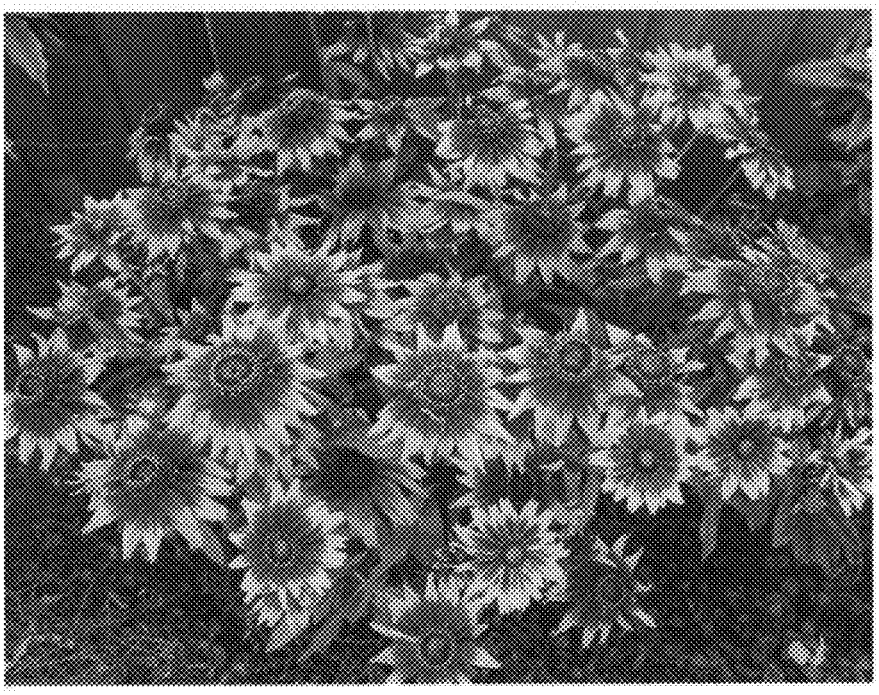

Botanical designation: *Echinacea purpurea* X *Rudbeckia hirta*.

Cultivar denomination: 'ET RDB 18-30'.

CROSS-REFERENCE TO A RELATED APPLICATION AND STATEMENT REGARDING PRIOR DISCLOSURES BY INVENTORS/APPLICANTS

This application claims priority to a European Community Plant Breeders' Rights application filed on Nov. 4, 2019, application number 2019/2797. There have been no offers for sale anywhere in the world prior to the effective filing date of this Application and no accessibility to one of ordinary skill in the art could have been derived from the printed Plant Breeder's Rights documents.

The Inventors/Applicants assert that no publications nor advertisements relating to sales, offers for sale or public distribution occurred more than one year prior to the effective filing date of this application. Any information about the claimed plant would have been obtained from a direct or indirect disclosure from the Inventors/Applicants. Inventors/Applicants claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Rudbeckia* plant, botanically known as *Echinacea purpurea* X *Rudbeckia hirta* and hereinafter referred to by the name 'ET RDB 18-30'.

The new *Rudbeckia* plant is a product of a planned breeding program conducted by the Inventors in Boijl, The Netherlands. The objective of the breeding program is to create new interspecific *Rudbeckia* plants with large long-lasting and attractive inflorescences on strong peduncles.

The new *Rudbeckia* plant originated from a cross-pollination made by the Inventors in Boijl, The Netherlands in August, 2015 of a proprietary selection of *Echinacea purpurea* identified as code designation T419, not patented, as the female, or seed parent with a proprietary selection of *Rudbeckia hirta* identified as code designation Q39, not patented, as the male, or pollen, parent. The new *Rudbeckia* plant was discovered and selected by the Inventors as a single flowering plant from within the progeny of the stated cross-pollination in a controlled environment in Boijl, The Netherlands in July, 2016.

Asexual reproduction of the new *Rudbeckia* by in vitro meristem culture in a controlled greenhouse environment in Boijl, The Netherlands since August, 2016 has shown that the unique features of this new *Rudbeckia* plant are stable and reproduced true to type in successive generations.

SUMMARY OF THE INVENTION

Plants of the new *Rudbeckia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ET RDB 18-30'. These characteristics in combination distinguish 'ET RDB 18-30' as a new and distinct *Rudbeckia* plant:

1. Relatively compact, upright to somewhat outwardly spreading and mounded plant habit.

2. Dense and bushy growth habit.
3. Freely flowering habit.
4. Long-lasting single-type inflorescences with yellow orange and dark red bi-colored ray florets positioned above the foliar plane on strong peduncles.
5. Good postproduction and garden performance.

Plants of the new *Rudbeckia* differ from plants of the female parent selection in the following characteristics:

1. Plants of the new *Rudbeckia* are shorter than plants of the female parent selection.
2. Inflorescences of plants of the new *Rudbeckia* are larger and more uniformly mounding than inflorescences of plants of the female parent selection.

Plants of the new *Rudbeckia* differ from plants of the male parent selection in the following characteristics:

1. Plants of the new *Rudbeckia* have smaller leaves than plants of the male parent selection.
2. Plants of the new *Rudbeckia* have smaller inflorescences than plants of the male parent selection.

Plants of the new *Rudbeckia* can be compared to *Rudbeckia hirta* X *Rudbeckia hybrida* 'ET RDB 603', disclosed in U.S. Plant Pat. No. 31,765. Plants of the new *Rudbeckia* differ primarily from plants of 'ET RDB 603' in the following characteristics:

1. Plants of the new *Rudbeckia* are broader than plants of 'ET RDB 603'.
2. Plants of the new *Rudbeckia* are more freely flowering than plants of 'ET RDB 603'.
3. Plants of the new *Rudbeckia* and 'ET RDB 603' differ in ray floret color as plants of the new *Rudbeckia* have yellow orange and dark red bi-colored ray florets whereas plants of 'ET RDB 603' have yellow orange and greyed orange bi-colored ray florets.

Plants of the new *Rudbeckia* can also be compared to *Rudbeckia hirta* X *Echinacea purpurea* 'ET-RDB 01', disclosed in U.S. Plant Pat. No. 25,221. Plants of the new *Rudbeckia* differ primarily from plants of 'ET-RDB 01' in the following characteristics:

1. Plants of the new *Rudbeckia* are broader than plants of 'ET-RDB 01'.
2. Plants of the new *Rudbeckia* are more freely flowering than plants of 'ET-RDB 01'.
3. Plants of the new *Rudbeckia* and 'ET-RDB 01' differ in ray floret color as plants of the new *Rudbeckia* have yellow orange and dark red bi-colored ray florets whereas plants of 'ET-RDB 01' have yellow, orange and reddish-colored ray florets.

BRIEF DESCRIPTION OF THE PHOTOGRAPHS

The accompanying photographs illustrate the overall appearance of the new *Rudbeckia* showing the colors as true as it is reasonably possible to obtain in colored reproductions of this type. Colors in the photographs may differ slightly from the color values cited in the detailed botanical description which accurately describe the colors of the new *Rudbeckia* plant.

The photograph on the first sheet (FIG. 1 of 2) comprises a side perspective view of a typical flowering plant of 'ET RDB 18-30' grown in a container.

Figure 2:
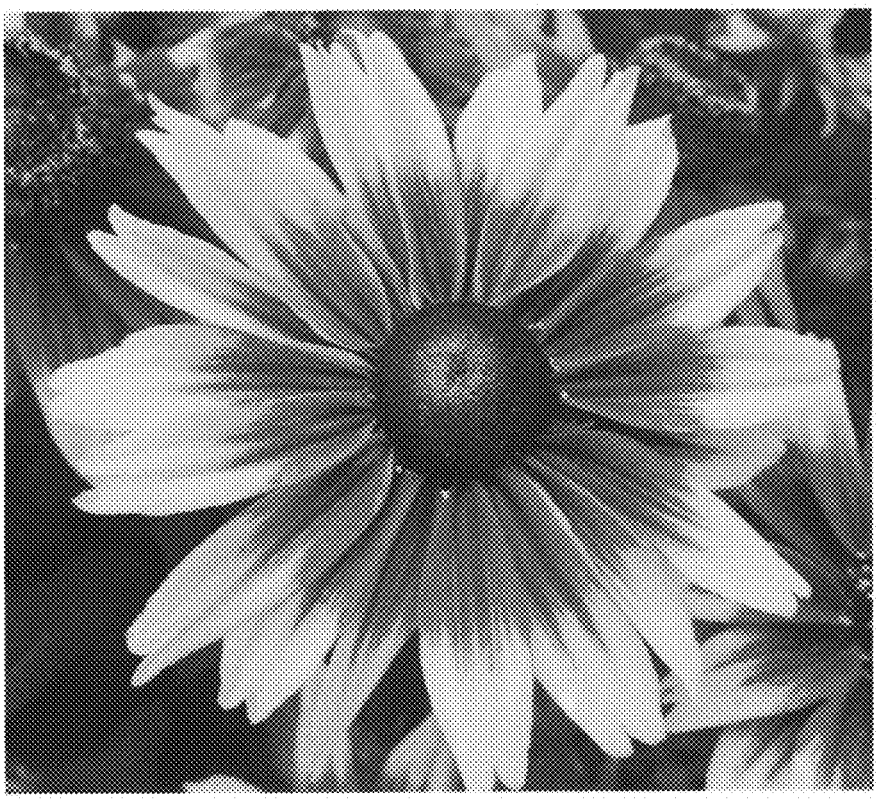

The photograph on the second sheet (FIG. 2 of 2) is a close-up view of a typical inflorescence of 'ET RDB 18-30'.

DETAILED BOTANICAL DESCRIPTION

The aforementioned photographs and following observations, measurements and values describe plants grown in 2.5-liter containers during the spring in an outdoor nursery in Boijl, The Netherlands and under cultural conditions typical of commercial *Rudbeckia* production. During the production of the plants, day temperatures averaged 16° C. and night temperatures averaged 10° C. Plants were one year old when the photographs and the detailed description were taken. In the following description, color references are made to The Royal Horticultural Society Colour Chart, 2001 Edition, except where general terms of ordinary dictionary significance are used.

Botanical classification: *Echinacea purpurea* X *Rudbeckia hirta* 'ET RDB 18-30'.

Parentage:

*Female, or seed, parent*.—Proprietary selection of *Echinacea purpurea* identified as code designation T419, not patented.

*Male, or pollen, parent*.—Proprietary selection of *Rudbeckia hirta* identified as code designation Q39, not patented.

Propagation:

*Type*.—By in vitro meristem culture.

*Time to initiate roots, summer*.—About seven to eight days at soil temperatures about 15° C. and ambient temperatures about 20° C.

*Time to produce a rooted young plants, summer*.—About four weeks at soil temperatures about 15° C. and ambient temperatures about 20° C.

*Root description*.—Medium in thickness; fleshy; color, close to 162C; actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial; compact, upright to somewhat outwardly spreading and mounded plant habit; dense and bushy appearance; vigorous growth habit; moderate growth rate.

*Plant height*.—About 50 cm to 60 cm.

*Plant width*.—About 80 cm to 90 cm.

*Lateral branches (peduncles)*.—Length: About 23 cm to 30 cm. Diameter: About 3 mm to 5 mm. Internode length: About 5 cm to 10 cm. Angle: Upright to somewhat outwardly spreading. Strength: Strong. Texture: Pubescent; rough. Color: Close to 144A.

Leaf description:

*Arrangement*.—Alternate, simple; sessile.

*Length*.—About 6 cm to 15 cm.

*Width*.—About 2 cm to 5 cm.

*Shape*.—Oblanceolate to obovate.

*Apex*.—Acute.

*Base*.—Attenuate.

*Margin*.—Dentate; undulate.

*Texture, upper and lower surfaces*.—Pubescent; rough.

*Venation pattern*.—Pinnate.

*Color*.—Developing leaves, upper surface: Close to 137B. Developing leaves, lower surface: Close to 137C. Fully developed leaves, upper surface: Close to 137A; venation, close to 145B. Fully expanded leaves, lower surface: Close to 137B; venation, close to 145B.

Inflorescence description:

*Type and arrangement*.—Single-type inflorescence form with lanceolate to oblanceolate-shaped ray florets and tubular disc florets; inflorescences borne on terminal and axillary peduncles above and beyond the foliar plane on strong peduncles; inflorescences face upright to outwardly; ray and disc florets arranged acropetally on a capitulum.

*Fragrance*.—None detected.

*Flowering season*.—Plants begin flowering about ten weeks after planting; long flowering period, plants flower continuously from mid-July until the end of October in The Netherlands.

*Inflorescence longevity*.—Good postproduction longevity with inflorescences lasting about eight to ten weeks on the plant; inflorescences persistent.

*Quantity of inflorescences*.—Freely flowering habit, typically more than 80 inflorescences developing per plant during the flowering season.

*Inflorescence buds*.—Height: About 1 cm to 2 cm. Diameter: About 1 cm. Shape: Round to ovoid. Color: Close to 145A.

*Inflorescences*.—Diameter: About 8 cm to 11 cm. Depth (height): About 1 cm to 3 cm. Diameter of disc: About 2 cm to 3 cm. Receptacle height: About 5 mm to 8 mm. Receptacle diameter: About 7 mm to 10 mm. Receptacle color: Close to 144A.

*Ray florets*.—Number of ray florets per inflorescence: About 16 to 18 arranged in a single whorl. Length: About 3 cm to 4 cm. Width: About 1.5 cm to 2 cm. Shape: Lanceolate to oblanceolate. Apex: Emarginate. Base: Attenuate. Margin: Entire. Texture, upper surface: Smooth, glabrous. Texture, lower surface: Rough, glabrous. Color: When opening, upper surface: Distally, close to 17A; proximally, close to 175A. When opening, lower surface: Close to 14A overlain with close to 145B. Fully opened, upper surface: Distally, close to 17A; proximally, close to 183A; venation, similar to lamina; color does not change with development. Fully opened, lower surface: Close to 14A overlain with close to 145B; venation, similar to lamina; color does not change with development.

*Disc florets*.—Arrangement: Numerous disc florets massed at center of receptacle. Length: About 2 cm to 3 cm. Width: About 1 mm to 2 mm. Shape: Tubular, elongated. Apex: Obtuse. Color, when opening: Apex: Close to N186C. Mid-section: Close to 145B tinged with close to N186C. Base: Close to 145B. Color, fully opened: Apex: Close to N186C. Mid-section: Close to N186C. Base: Close to N186C.

*Phyllaries*.—Number of phyllaries per inflorescence: About 20 to 30 arranged in about three whorls. Length: About 1 cm to 3 cm. Width: About 2 mm to 5 mm. Shape: Lanceolate. Apex: Acute to obtuse. Base: Fused to receptacle. Margin: Entire; slightly undulate. Texture, upper and lower surfaces: Rough, pubescent. Color, upper surface: Close to 137A. Color, lower surface: Close to 137B.

*Reproductive organs*.—Androecium (present on ray and disc florets): Quantity per floret: Numerous. Filament length: About 1 mm to 2 mm. Filament color: Close to N186A. Anther shape: Round. Anther length: About 1 mm to 2 mm. Anther color: Close to N186A. Pollen amount: Abundant. Pollen color: Close to 12A. Gynoecium (present only on disc florets): Pistil length: About 2 mm to 3 mm. Stigma shape: Two-parted. Stigma color: Close to N187A. Style length: About 1 mm to 2 mm. Style color: Close to N187A.

*Seeds and fruits*.—To date, seed and fruit production has not been observed on plants of the new *Rudbeckia*.

Pathogen & pest resistance: To date, plants of the new *Rudbeckia* have not been observed to be resistant to pathogens and pests common to *Rudbeckia* plants.

Garden performance: Plants of the new *Rudbeckia* have been observed to have good garden performance and to tolerate wind, rain and temperatures from about −20° C. to about 40° C.

It is claimed:

1. A new and distinct *Rudbeckia* plant named 'ET RDB 18-30' as illustrated and described.

* * * * *